United States Patent
Brierley

Patent Number: 6,004,302
Date of Patent: Dec. 21, 1999

[54] CANNULA

[76] Inventor: Lawrence A. Brierley, 4772 Spring Rd., Victoria, B.C., Canada, V8X 3X1

[21] Appl. No.: 08/921,657

[22] Filed: Aug. 28, 1997

[51] Int. Cl.$^6$ .................................................. A61M 5/00
[52] U.S. Cl. ........................... 604/264; 604/239; 604/523
[58] Field of Search ..................... 604/264, 272, 604/273, 274, 239, 523

[56] References Cited

U.S. PATENT DOCUMENTS

| | | | |
|---|---|---|---|
| 3,788,327 | 1/1974 | Donowitz et al. | 604/239 X |
| 4,331,130 | 5/1982 | Lewicky | 128/1 |
| 4,340,037 | 7/1982 | Lewicky | 128/1 |
| 4,670,008 | 6/1987 | Von Albertini | 604/165 |
| 4,781,675 | 11/1988 | White | 604/10 |
| 4,808,170 | 2/1989 | Thornton et al. | 604/274 |
| 5,032,111 | 7/1991 | Morris et al. | 604/23 |
| 5,364,374 | 11/1994 | Morrison et al. | 604/272 |

OTHER PUBLICATIONS

Page, R.N. et al, 1968, "Maintenance of the Anterior Chamber in Intraocular Surgery: Instrurments and Techniques", pp. 161–173.

*Primary Examiner*—John D. Yasko
*Attorney, Agent, or Firm*—Brown, Pinnisi & Michaels, P.C.

[57] ABSTRACT

A cannula has a shank and a tip which is elliptical in cross-section having radially extending crescent-shaped fins for engaging the tissue lining the tunnel of an incision. The cannula is thus retained in position and is not forced out with fluid pressure or by traction on attached tubing with eye movements or inadvertently hooking instruments. The cannula is rotated to disengage the fins from the incision by stretching the incision with the major axis of the elliptical tip. The cannula of the present invention is suitable for penetration of organs or vessels under fluid pressure for surgical procedures, in particular for ophthalmic surgical procedures.

5 Claims, 4 Drawing Sheets

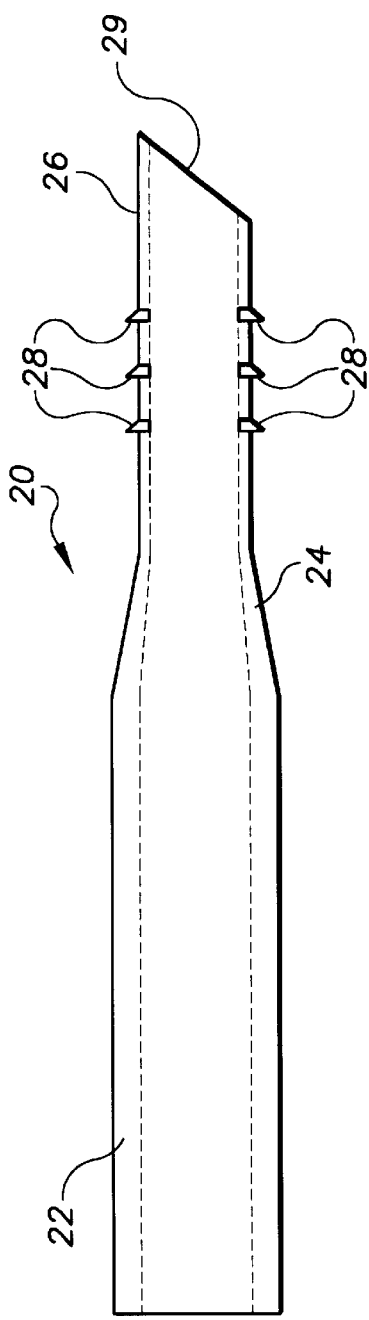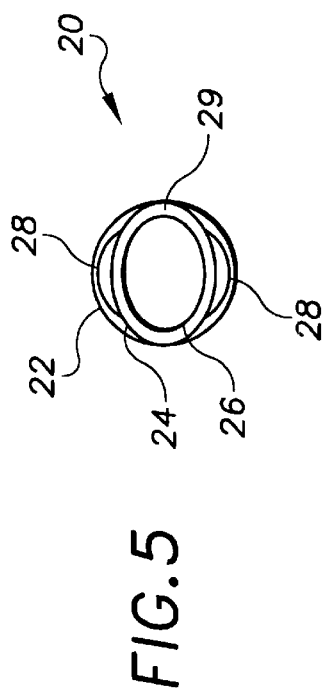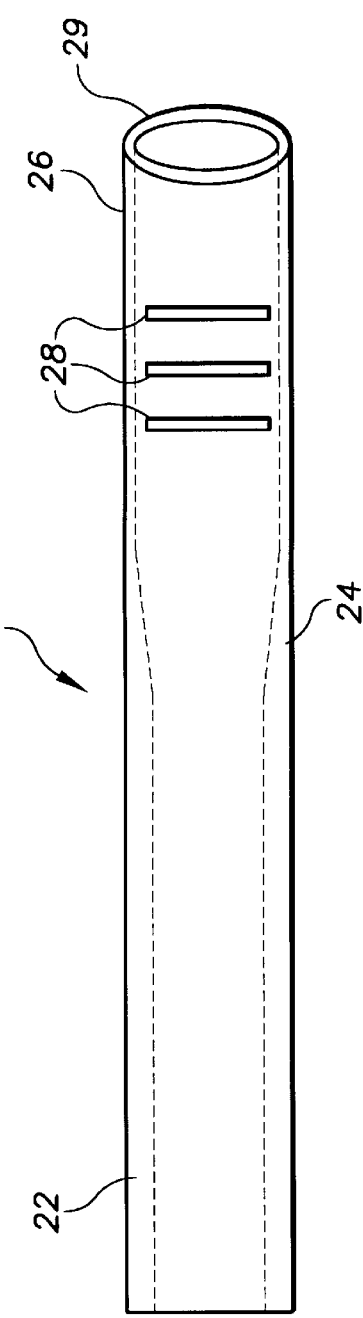

CANNULA

FIELD OF THE INVENTION

The present invention relates to a cannula for surgical procedures and, in particular, for ophthalmic surgical procedures.

BACKGROUND OF THE INVENTION

In surgical procedures, it is often desirable to use a cannula to penetrate an organ or vessel under fluid pressure. For example, a number of ophthalmic surgical procedures involve penetrating the chambers of the eye with surgical instruments. The anterior chamber of the eye contains a physiologic fluid and is located between the cornea and the lens of the eye. The vitreous chamber between the lens and the retina is filled with vitreous humour, a transparent gel-like substance. The configuration of the ocular chambers is maintained by fluid pressure.

When surgery is performed, the penetration of a surgical instrument and, to a greater extent, the removal of fragments of ocular tissue, such as cataractous tissue or other diseased tissue, by aspiration results in loss of fluid and pressure in the respective ocular chamber. Furthermore, it will be appreciated by those skilled in the art that, under surgical conditions, there may be fluctuations in pressure in the ocular chambers due to surgical manipulations, such as starting or enlarging an incision, inserting instruments into the incision, pulling on ocular muscles or tightening of sutures.

Loss of fluid and pressure in the ocular chambers during ophthalmic surgical procedures can cause at least partial collapse of the chamber making it difficult to manipulate an instrument within the eye without endangering vulnerable structures such as the corneal endothelium, the lens capsule and the iris. Clearly, it is desirable to maintain the integrity and internal pressure of the ocular chambers during and after surgery.

One accepted technique for maintaining pressure in the ocular chambers is to introduce fluid, such as air, saline solution or other liquid or gas, into the anterior chamber and/or the vitreous chamber either during the ophthalmic surgical procedure or at the time of closure of the incision(s). The infusion of fluid helps to maintain a positive pressure and the normal configuration of the ocular chamber during surgery. Furthermore, control of intraocular pressure during surgery helps to minimize danger to the eye during and after surgery. Positive pressure stretches open the pupil permitting better visualization of posterior structures. It also ensures that any flow across a wound is outward, not inward, reducing the risk of entry of foreign matter or bacteria.

Fluid is typically introduced to the ocular chambers via a so-called chamber maintainer cannula inserted through a surgical stab wound or other incision. The chamber maintainer cannula is connected via silicone elastomer tubing or other suitable tubing to a container holding infusion fluid. The flow of infusion fluid through the chamber maintainer cannula is controlled by the surgeon or an assistant in response to a surgeon's instructions, for example by operation of a foot pedal, by fingertip control or by altering the height of an infusion bottle.

In retinal surgery, the chamber maintainer cannula is inserted into the vitreous chamber through the sclera, which is a fibrous tissue intermixed with fine elastic fibres. For anterior segment eye surgery, the cannula is inserted directly through the peripheral cornea or via the anterior sciera to the peripheral cornea into the anterior chamber. The cornea, in contrast with the sclera, has a thick central layer which is fibrous, tough and unyielding.

One known chamber maintainer cannula is a smooth-walled uniform diameter shaft which may have an angled tip to facilitate entry through an incision made in the sclera and/or the peripheral cornea. The cannula is held in position by sutures. However, the sutures require an additional surgical procedure. Moreover, the patient is further traumatized by the suturing. One attempt to overcome the need for sutures is to provide a cannula which has an etched surface. However, the present inventor and other practitioners have found that the etched cannula does not perform satisfactorily and, especially upon introduction of fluid, still requires the use of sutures to hold the cannula in position. Furthermore, even with the use of sutures to secure the smooth-walled and etched cannulae, there is some back-flow of fluid from the pressurized ocular chambers. This problem is acknowledged in "Maintenance of the Anterior Chamber in Intraocular Surgery: Instruments and Techniques" (Page, R. N. et al *Trans Pacific Coast Oto-Ophthalmolopical Society* 161–173; 1968).

U.S. Pat. No. 4,331,130 (Lewicky, May 25, 1982) relates to a device for preventing collapse of the anterior chamber during ophthalmic procedures comprising a pneumatic pump, a liquid pump and a fluid flow connection for connecting the pumps to an infusion terminal. The infusion terminal has a shank with a tapered rounded head and an axially extending central fluid-flow passageway for the introduction of fluids into the eye. The shank has helical external screw threads or annular detents, rings or circular ribs which extend outwardly therefrom. Lewicky teaches that the maximum outside diameter of the threads or detents, as well as the shank, should be smaller than the diameter of the surgical opening. Specifically, the opening in the eye should be one to two gauge sizes larger than the outside diameter of the threads or rings.

The method for preventing collapse of the anterior chamber of the eye during ophthalmic surgical procedures is described in U.S. Pat. No. 4,340,037 (Lewicky, Jul. 20, 1982). According to the method of Lewicky, a partial-thickness groove is made in the sclera or external coat of the eye and two sutures are pre-placed in this groove. A 22-gauge disposable needle is used to create a full-thickness corneal tract to the anterior chamber. The needle is withdrawn and a 23-gauge infusion terminal is inserted through the corneal tract. The infusion terminal is connected by a fluid line to a pump for infusion of a balanced salt solution by control of foot pedals by the surgeon.

The present inventor has personal experience with the Lewicky infusion terminal and has found that the terminal stays in position well and reduces the back-flow around the terminal, but only if the terminal is tightly wedged into the entry wound. However, the present inventor has also found the terminal awkward to insert unless the stab wound is large. The size of the stab wound or incision is critical for application of Lewicky's terminal since the threads or rings and the shank are of a uniform outside diameter along the length of the terminal and because, as previously indicated, the cornea is a rigid structure. It will be appreciated by those skilled in the art that, if the stab wound is too small, insertion of the terminal is very difficult. If the stab wound if too large, the fit between the terminal and the wound is too loose to retain the terminal snugly. A loose fit between the wound and the terminal can result in back-flow of fluid out of the wound, particularly during infusion of fluids into the ocular chambers. Moreover, the terminal can be dislodged from the wound, in which case the surgical operation must be either interrupted or terminated.

In spite of the numerous advantages of using a chamber maintainer, as discussed above, few eye surgeons working in the anterior chamber routinely use one, relying instead on disposable viscoelastic agents to form the anterior chamber and to protect intraocular structures. However, these are expensive (adding many millions of dollars annually to the cost of cataract surgery alone in the United States) and they can block aspiration of anterior chamber fluid during ultrasonic fragmentation of the nucleus in cataract surgery resulting in severe wound burns. The viscoelastic agents are also very difficult to completely extract from the eye and can raise the post-operative intraocular pressure resulting in a transient but nevertheless potentially vision-damaging form of glaucoma.

The main reasons why surgeons eschew the use of a chamber maintainer are inconvenience and difficulty with their insertion and lack of confidence in their retention.

It is an object of the present invention to provide a cannula which will not become unintentionally dislodged once in position.

It is another object of the present invention to provide a cannula which is easily inserted and removed.

It is a further object of the present invention to eliminate the requirement for sutures to hold the cannula in position.

SUMMARY OF THE INVENTION

According to one aspect of the present invention, there is provided a cannula comprising a shank, a tip which is elliptical in cross-section having a major axis and a minor axis, and means for engaging tissue lining an incision on the outer surfaces of the elliptical tip, the means for engaging tissue positioned on the perimeter of the ellipse about the minor axis.

BRIEF DESCRIPTION OF THE DRAWINGS

In drawings which illustrate embodiments of the present invention:

FIG. 4 is a side elevational view of another embodiment of the cannula of the present invention;

FIG. 5 is a front elevational view of the cannula of FIG. 4;

FIG. 6 is a top plan view of the cannula of FIG. 4;

DETAILED DESCRIPTION OF THE PREFERRED EMBODIMENTS

Figure 1:
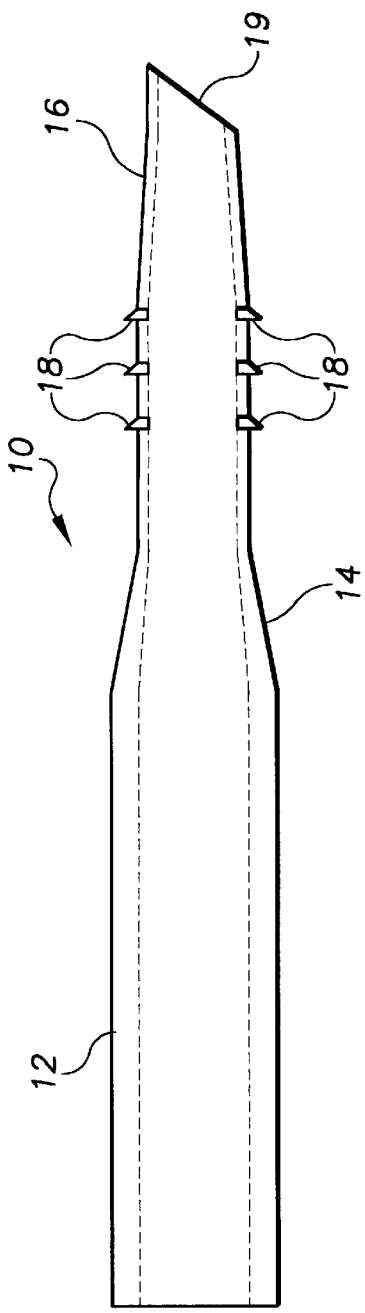
FIG. 1 is a side elevational view of one embodiment of the cannula of the present invention.
Figure 2:
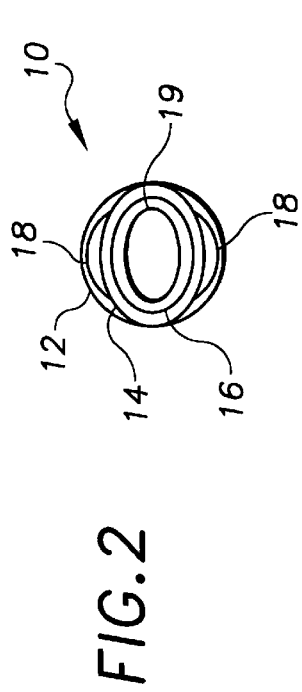
FIG. 2 is a front elevational view of the cannula of FIG. 1.
Figure 3:
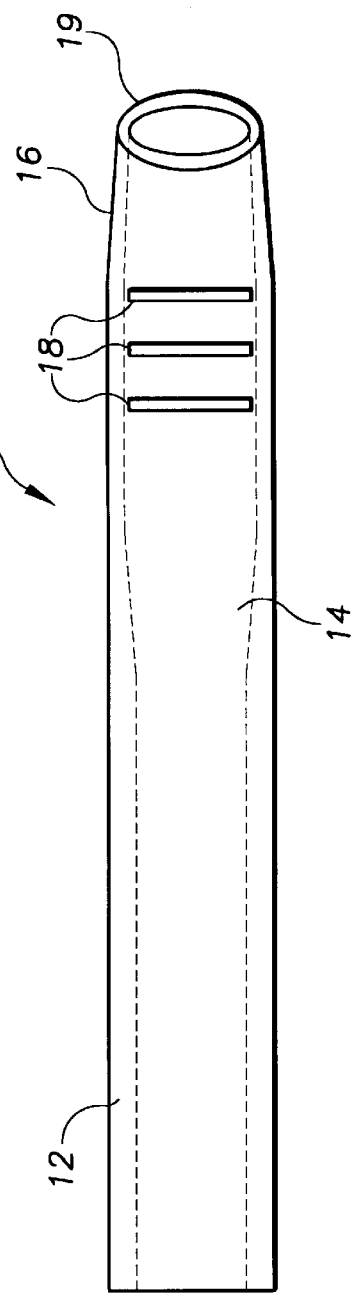
FIG. 3 is a top plan view of the cannula of FIG. 1.
Figure 7:
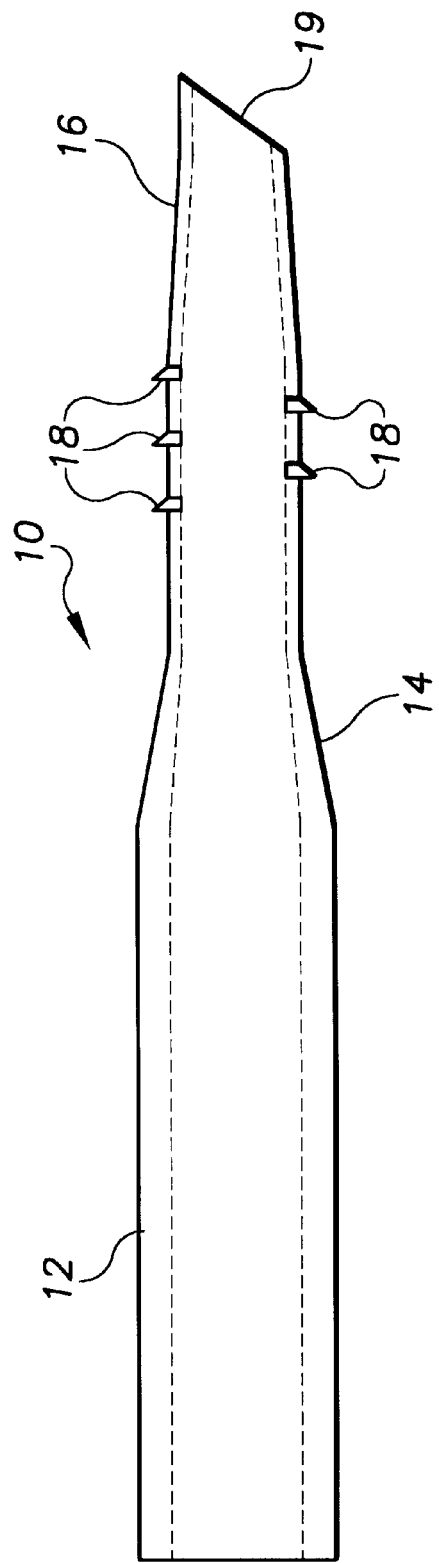
FIG. 7 is a side elevational view of yet another embodiment of the cannula of the present invention.

Referring now to FIGS. 1, 2 and 3, a cannula 10 has a cylindrical shank 12, a tapered neck 14 and a tip 16 which is elliptical in cross-section. The shank 12 can be adapted, as shown, for connection via silicone elastomer tubing or other suitable tubing to a container holding infusion fluid, such as air, saline solution or other gases or liquids. The tapered neck 14 is tapered on the top and bottom from the cylindrical shank 12 to the elliptical tip 16.

The tip 16 has crescent shaped fins 18 extending radially outwardly from the tip 16 and an angled face 19. In the embodiment shown in FIGS. 1, 2 and 3, a portion of the tip 16 proximate the face 19 is tapered on the top and bottom surfaces. The angled face 19 of the tip 16 allows for easier insertion into an incision or surgical stab wound in the wall of the ocular chamber. The crescent shaped fins 18 are angled to allow the tip 16 to be easily inserted. The fins 18 retain the cannula 10 in position during the surgical procedure.

Figure 8:
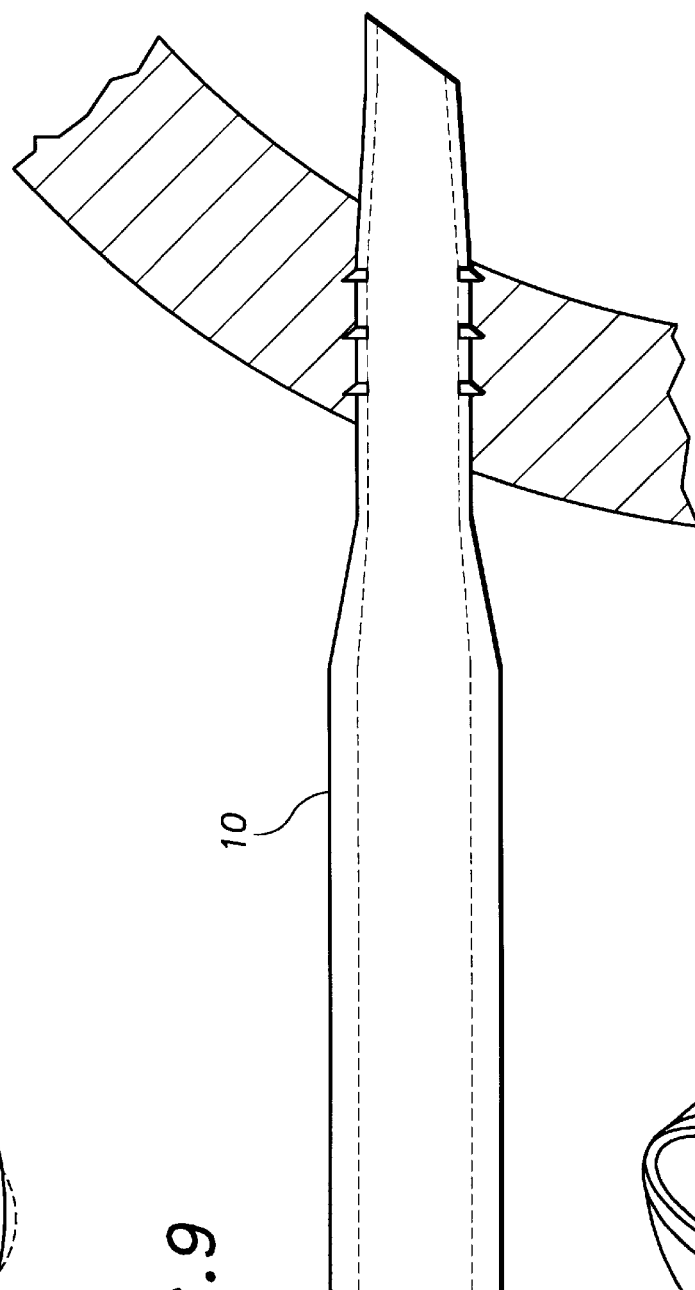
FIG. 8 illustrates schematically how the cannula of the present invention is secured once inserted in an incision.

In the embodiment shown in FIGS. 1, 2 and 3, there are three pairs of fins 18. However, it is not necessary that there be three pairs of fins 18. The cannula of the present invention is operational with at least one pair of fins 18. The fins may also be arranged in a staggered fashion as shown in FIG. 8.

FIGS. 4, 5 and 6 depict another embodiment of a cannula 20 of the present invention. The cannula 20 has a cylindrical shank 22, a tapered neck 24 and a tip 26 which is elliptical in cross-section. The shank 22 can be adapted, as shown, for connection via silicone elastomer tubing or other suitable tubing to a supply of infusion fluid. The tapered neck 24 is tapered from the cylindrical shank 22 to the elliptical tip 26. The tip 26 has crescent shaped fins 28 and an angled face 29. In the embodiment shown in FIGS. 4, 5 and 6, the tip 26 is not tapered.

As in the first embodiment described with reference to FIGS. 1, 2 and 3, there are three pairs of crescent shaped fins 28 extending radially outwardly from the tip 26 of the cannula 20. The cannula of the present invention is operational with at least one pair of fins 28. The fins 28 may also be arranged in a staggered fashion as shown in FIG. 8.

The angled face of the tip 16, 26 allows the cannula 10, 20 to be easily inserted into an incision in the wall of the particular ocular chamber. The tip 16, 26 is preferably at least semi-sharp to enter the incision or stab wound. It will be appreciated by those skilled in the art that once a stab wound is made and the instrument with which the wound is made is withdrawn, the incision or stab wound contracts. Accordingly, the tip 16, 26 should have some degree of sharpness to re-enter the incision or stab wound. However, it is not necessary that the tip 16, 26 be so sharp so as to have a cutting edge.

Figure 9:
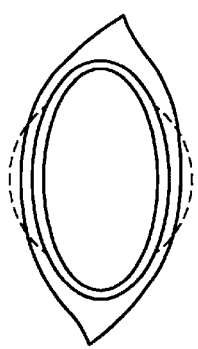
FIG. 9 is a side elevational view of the inserted cannula of FIG. 8.

The tips 16, 26 of the cannulae 10, 20 are smooth and can be easily pushed into the incision. As the tip 16, 26 is inserted, the fins 18, 28 engage the tissue lining the tunnel of the incision, as shown in FIG. 9. The fins 18, 28 hold the cannula 10, 20 in position in the incision and reduce the likelihood that the cannula 10, 20 will be pushed out of the incision during the surgical procedure. The elliptical circumference of the tip 16, 26 ensures that the cannula will not easily rotate within the flat stab wound.

The tapered portion of the tip 16 of the cannula 10 also facilitates insertion into incisions or stab wounds. While the tip of the cannula is preferably tapered as shown in the embodiment shown in FIGS. 1, 2 and 3, the tip is also operational when it is not tapered, as shown in the embodiment of FIGS. 4, 5 and 6.

The tapered neck 14, 24 allows the tip 16, 26 to be wedged into the wound without the leading point of the angled face 19, 29 extending so far into the anterior chamber as to endanger intraocular structures. The neck 14, 24 may thus serve as a "stopper" and an enhanced seal.

The cannula 10, 20 thus seals the incision in the wall of the organ or vessel, such as the ocular chamber and minimizes any back-flow of fluid from the chamber. Accordingly, the cannula 10, 20 is held in position in the incision and the risk of becoming unintentionally dislodged, by traction on attached tubing with eye movements or inadvertently hooking instruments, during the surgical procedure is minimized.

The tip 16, 26 of the cannula 10, 20 is elliptical in cross-section so that the cannula can be easily disengaged. As will be described in more detail below, rotation of the cannula, so that the major axis of the ellipse is perpendicular to the incision, disengages the fins 26, 28 from the tissue lining the tunnel of the incision.

The shank 12, 22 is shown as being cylindrical in the embodiments shown in the drawings. However it is not necessary that the shank 12, 22 be cylindrical. For example, the shank 12, 22 may be elliptical in cross-section. It is also not necessary that the shank 12, 22 be of a greater diameter than the tip 16, 26.

The cannula 10, 20 of the present invention is particularly suited for ophthalmic surgical procedures and the discussion below will refer to this application. However, it will be understood by those skilled in the art that the cannula 10, 20 of the present invention can likewise be used in surgical procedures in other organs or vessels under fluid pressure, such as a major blood vessel. For example, the cannula 10, 20 of the present invention may be used to anchor any infusion device, aspiration device or combination thereof in the wall of such organs or vessels.

In use, an incision is made in the wall of the desired ocular chamber, for example by inserting a needle into the wall to cause a stab wound or by cutting a slit with a surgical blade. The tip 16, 26 of the cannula 10, 20 is smooth and can be easily pushed into the incision. Once inside the ocular chamber, the tissue contracts around the tip 16, 26 allowing the fins 18, 28 to penetrate into the substance of the wall of the incision (either the cornea or the sclera). The inserted tip is illustrated in FIGS. 8 and 9.

Figure 10:
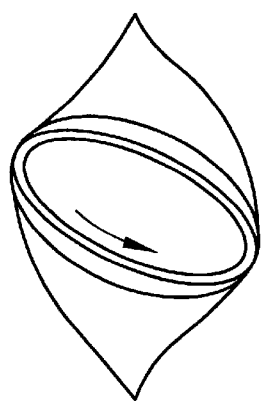
FIG. 10 illustrates schematically how the cannula of the present invention is disengaged from the incision of FIG. 8.

When it is desired to remove the cannula 10, 20 from the ocular chamber, the cannula 10, 20 is rotated to disengage the fins 18, 28 from the incision, as shown in FIG. 10. As the cannula 10, 20 is rotated, the elliptical shape of the tip 16, 26 stretches the incision so that the fins 18, 28 are disengaged from the tissue lining the tunnel of the incision. The cannula can then be pulled out of the incision. Sutures are not required to seal the incision in the cornea because, once the cannula 10, 20 is removed, normal intraocular pressure is re-established and this forces the floor of the tunnel against the roof of the tunnel preventing egress of fluid. Very soon healing begins and this ultimately seals the tunnel definitively. Sutures may be required to close an incision in the sclera because the sclera is thinner and more elastic than the cornea making it difficult to fashion a long oblique tunnel. It will be understood by those skilled in the art that the shorter and more perpendicular an incision is to the surface of the tunnel, the less self-sealing it will be.

The cannula 10, 20 of the present invention is connected via silicone elastomer tubing to a source of infusion fluid. For example, the cannula 10, 20 may be used with an anterior chamber maintainer as described in U.S. Pat. No. 4,331,130 (Lewicky).

The cannula 10, 20 may also be useful for aspiration or a combination of aspiration and infusion by the provision of an inner tube inside the cannula or by otherwise dividing the inner bore of the cannula into two channels, for example with an internal wall. The shank could be formed in the shape of a Y.

It will be appreciated by those skilled in the art that the cannula of the present invention could also be useful as a cannula for an implantable device for drug delivery, of the type described in U.S. Pat. No. 4,781,675 (White, T. C., Nov. 1, 1988). White's device includes a tube having a first end which is inserted into the cavity of the eye. The tube has a flange which is attached to the sclera by sutures. A one-way valve is positioned within the tube between the inlet and outlet ends to allow fluid flow only toward the outlet end. A compressible reservoir is filled with infusion fluid and allows for convenient digital manipulation to express infusion fluid outwardly from the reservoir. The cannula of the present invention would obviate the requirement for sutures.

Changes and modifications in the specifically described embodiments can be carried out without departing from the scope of the invention which is intended to be limited only by the scope of the appended claims.

I claim:

1. A cannula comprising a shank, a tip which is elliptical in cross-section having a major axis and a minor axis, and means for engaging tissue lining an incision on the outer surfaces of the elliptical tip, the means for engaging tissue positioned on the perimeter of the eiiipticai tip about the minor axis.

2. A cannula according to claim 1, wherein the means for engaging tissue is a pair of opposing radially extending fins substantially bisected by the minor axis on the perimeter of the elliptical tip.

3. A cannula according to claim 1, wherein the means for engaging tissue is opposing radially extending fins substantially bisected by the minor axis on the perimeter of the elliptical tip and staggered along the length of the elliptical tip.

4. A cannula according to claim 1, wherein a portion of the elliptical tip is tapered toward a distal end thereof.

5. A cannula according to claim 1, wherein the elliptical tip has an angled face at the distal end thereof.

* * * * *